(12) United States Patent
Meglan

(10) Patent No.: US 11,583,356 B2
(45) Date of Patent: Feb. 21, 2023

(54) CONTROLLER FOR IMAGING DEVICE

(71) Applicant: Covidien LP, Mansfield, MA (US)

(72) Inventor: Dwight Meglan, Westwood, MA (US)

(73) Assignee: COVIDIEN LP, Mansfield, MA (US)

( * ) Notice: Subject to any disclaimer, the term of this patent is extended or adjusted under 35 U.S.C. 154(b) by 595 days.

(21) Appl. No.: 16/615,589

(22) PCT Filed: May 7, 2018

(86) PCT No.: PCT/US2018/031383
§ 371 (c)(1),
(2) Date: Nov. 21, 2019

(87) PCT Pub. No.: WO2018/217436
PCT Pub. Date: Nov. 29, 2018

(65) Prior Publication Data
US 2020/0155256 A1    May 21, 2020

Related U.S. Application Data

(60) Provisional application No. 62/511,490, filed on May 26, 2017.

(51) Int. Cl.
*G09G 5/00* (2006.01)
*A61B 34/00* (2016.01)
*A61B 34/37* (2016.01)
*A61B 90/00* (2016.01)

(52) U.S. Cl.
CPC .............. *A61B 34/74* (2016.02); *A61B 34/37* (2016.02); *A61B 90/361* (2016.02); *A61B 2034/741* (2016.02); *A61B 2034/742* (2016.02)

(58) Field of Classification Search
CPC .... A61B 2017/00221; A61B 2034/741; A61B 2034/742; A61B 34/37; A61B 34/74; A61B 90/361; A61B 90/37; A61B 90/53
See application file for complete search history.

(56) References Cited

U.S. PATENT DOCUMENTS

| 8,828,023 B2 | 9/2014 | Neff et al. |
| 8,880,223 B2 | 11/2014 | Raj et al. |
| 9,827,060 B2 | 11/2017 | Jagga |

(Continued)

FOREIGN PATENT DOCUMENTS

KR    1020050039799    4/2005

OTHER PUBLICATIONS

Extended European Search Report dated Jan. 12, 2021 corresponding to counterpart Patent Application EP 18806156.8.

(Continued)

*Primary Examiner* — Insa Sadio
(74) *Attorney, Agent, or Firm* — Carter, DeLuca & Farrell, LLP

(57) ABSTRACT

A controller includes an attachment member and an interface. The attachment member is configured to secure the controller to a hand of a clinician. The interface includes a first controller that is configured to operate an imaging device of a surgical system. The controller can secure about a finger of a clinician and be engagable by a thumb of the same hand of the clinician. Alternatively, the controller can be disposed in a palm of a hand of a clinician and engaged by a finger of the hand.

7 Claims, 3 Drawing Sheets

(56) References Cited

U.S. PATENT DOCUMENTS

| | | | | |
|---|---|---|---|---|
| 2001/0000433 A1* | 4/2001 | Russell | ................... | G06F 21/83 |
| | | | | 345/157 |
| 2008/0300489 A1 | 12/2008 | Schutz et al. | | |
| 2012/0071892 A1 | 3/2012 | Itkowitz et al. | | |
| 2012/0105315 A1 | 5/2012 | Wilson et al. | | |
| 2015/0245876 A1 | 9/2015 | Kim et al. | | |
| 2015/0297768 A1* | 10/2015 | Bettles | ...................... | A61L 2/10 |
| | | | | 250/455.11 |
| 2016/0015476 A1 | 1/2016 | Jagga | | |
| 2016/0175057 A1* | 6/2016 | Ibach | ................... | A61B 1/0661 |
| | | | | 600/103 |
| 2018/0168758 A1 | 6/2018 | Lutzow et al. | | |

OTHER PUBLICATIONS

International Search Report dated Aug. 29, 2018 and Written Opinion completed Aug. 29, 2018 corresponding to counterpart Int'l Patent Application PCT/US18/31383.
Chinese First Office Action dated Jul. 19, 2022 corresponding to counterpart Patent Application CN 201880033756.2.

\* cited by examiner

CONTROLLER FOR IMAGING DEVICE

CROSS-REFERENCE TO RELATED APPLICATIONS

This application is a National Stage Application of PCT/US2018/031383, filed May 7, 2018 under 35USC § 371 (a), which claims benefit of and priority to U.S. Provisional Patent Application Ser. No. 62/511,490 filed May 26, 2017, the disclosures of each of the above-identified applications are hereby incorporated by reference in their entirety.

BACKGROUND

Robotic surgical systems such as teleoperative systems are used to perform minimally invasive surgical procedures that offer many benefits over traditional open surgery techniques, including less pain, shorter hospital stays, quicker return to normal activities, minimal scarring, reduced recovery time, and less injury to tissue.

Robotic surgical systems can have a number of robotic arms that move attached instruments or tools, such as an image capturing device, a stapler, an electrosurgical instrument, etc., in response to movement of input devices by a surgeon viewing images captured by the image capturing device of a surgical site. During a robotic surgical procedure, each of the tools is inserted through an opening, either natural or an incision, into the patient and positioned to manipulate tissue at a surgical site. The openings are placed about the patient's body so that the surgical instruments may be used to cooperatively perform a robotic surgical procedure and the image capturing device (e.g., an endoscope) may view the surgical site.

Robotic surgical systems can typically include a display that displays images, graphical representations, or combinations thereof of the surgical site such that the surgeon operating the robotic surgical system can accurately manipulate the tools within the surgical site with the user interface. During a surgical procedure the surgeon may require a change in the view point of the surgical site requiring manipulation or adjustment of the image capturing device. Generally, manipulation or adjustment of the image capturing device requires a surgeon to remove their hands from the controls of a tool to adjust the image capturing device or to request that an assistant manipulates or adjusts the image capturing device. Both of these options cause a discontinuity in and/or a delay during the robotic surgical procedure.

Accordingly there is a need for methods and/or devices for redirecting the viewpoint of an image capturing device during a robotic surgical procedure in a more efficient manner.

SUMMARY

This disclosure relates generally to a hand-based controller that allows a clinician to redirect the viewpoint of an image capturing device during a robotic surgical procedure without requiring the clinician to remove their hands from the controls of the surgical tools.

In an aspect of the present disclosure, a controller includes an attachment member and an interface. The attachment member is configured to secure the controller to a hand of a clinician. The interface includes a first controller that is configured to operate an imaging device of a surgical system.

In aspects, the attachment member has a ring-like shape and is configured to secure the controller to a digit of the clinician. The attachment member may be adjustable. The first controller may be a joystick.

In some aspects, the interface includes a second controller that has first and second positions. The first controller may have a first mode when the second controller is in the first position and the first controller may have a second mode when the second controller is in the second position. The first controller may be configured to operate pan functions of the imaging device in the first mode and may be configured to operate rotation and zoom functions of the imaging device in the second mode. The second controller may be a button or a switch. Alternatively, the second controller may be a touch-sensitive surface that is engagable by a digit of the hand of the clinician.

In certain aspects, the first controller is a touch-sensitive surface that is engagable by a digit of the hand of the clinician. The interface may be disposed in the palm of the handle of the clinician. Additionally or alternatively, the interface may be disposed on a glove worn on the hand of a clinician.

In another aspect of the present disclosure, a robotic surgical system includes a processing unit, a surgical robot, and a user interface. The surgical robe is configured to receive commands from the processing unit and includes a first tool and an imaging device. The first tool is supported by a first linkage and the imaging device is supported by an imaging linkage. The user interface is in communication with the processing unit and is configured to operate the surgical robot. The user interface includes a display, a first control arm, and an image controller. The first control arm is configured to operate the first tool. The image controller includes an attachment member and an interface. The attachment member is configured to secure the image controller to a handle of a clinician engaged with the first control arm. The interface includes a first controller that is configured to operate the imaging device to manipulate a graphical representation on the display.

In aspects, the image controller may be in wireless communication with the processing unit. The surgical tool may include a second tool that is supported by a second linkage and the user interface may include a second control arm that is configured to operate the second tool. The first control arm may operate the first tool, the second control arm may operate the second tool, and the image controller may operate the imaging device simultaneously and independent of one another.

In another aspect of the present disclosure, a method of operating an imaging device of a robotic surgical system includes engaging a control arm of a user interface with a hand to operate a first tool of a surgical robot and engaging an image controller with a digit of the handle engaged with the control arm to operate an imaging device of the surgical robot. The image controller is attached to the hand of the clinician.

In aspects, engaging the image controller with a digit of the hand engaged with the control arm includes engaging the image controller with a digit of the hand engaged with the control arm. Engaging the image controller with the digit of the hand engaged with the control arm may include engaging the image controller with a thumb of the hand engaged with the control arm. The image controller may be supported on another digit of the hand.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
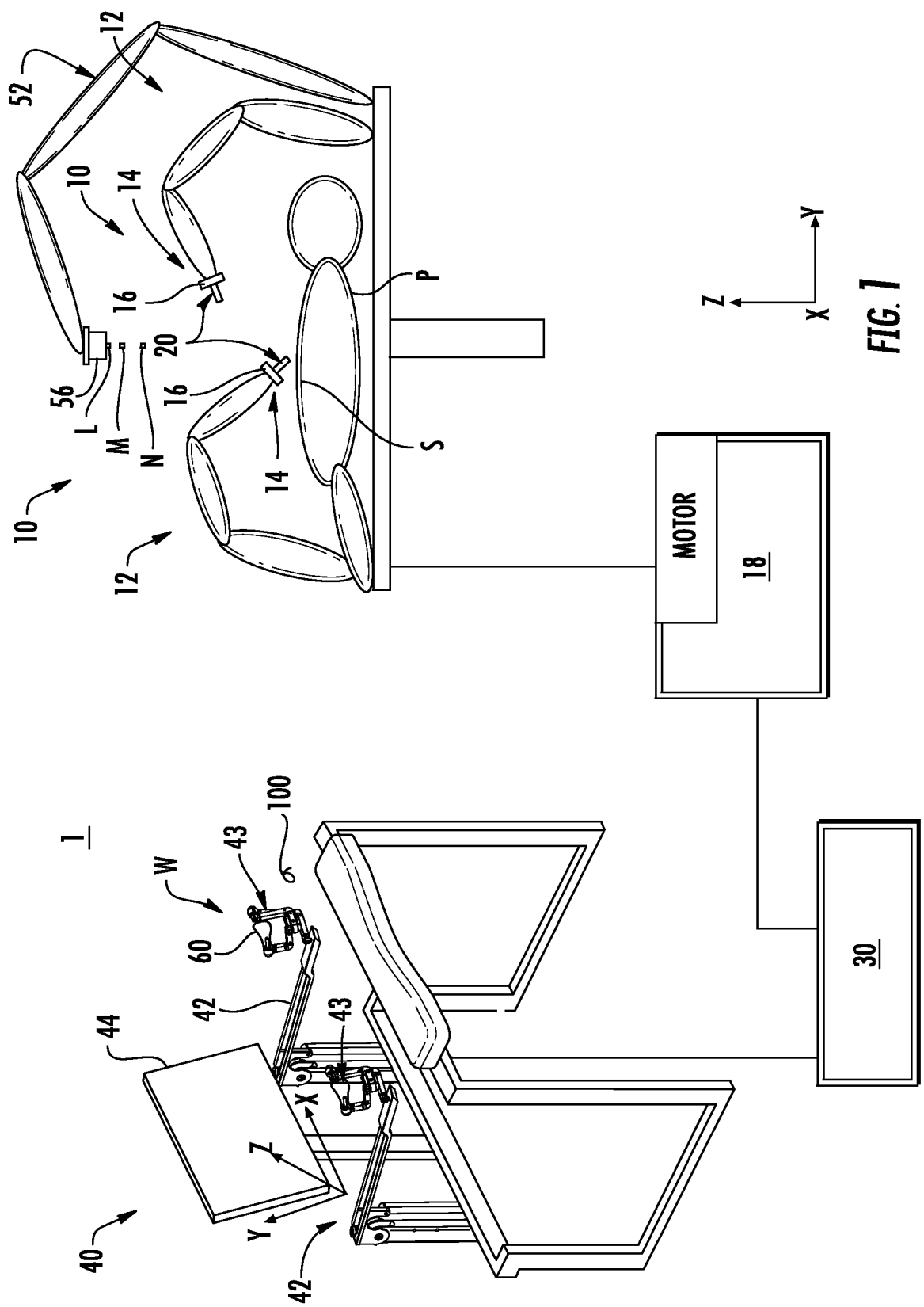
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician or surgical robot arm and the term "distal" refers to the portion of the device or component thereof that is farthest from the clinician or surgical robot arm. Throughout this description, the term "finger" refers to a digit of a hand of a clinician other than the thumb and the term "digit" refers to a finger or a thumb of a hand of a clinician.

This disclosure relates generally to an imaging controller that allows a clinician to redirect the viewpoint of an image capturing device during a robotic surgical procedure without requiring the clinician to remove their hands from the controls of the surgical tools. By not requiring the clinician to redirect their attention from surgical tools, the efficiency of a robotic surgical procedure can be improved resulting in lower costs and improved surgical outcomes.

In embodiments, the imaging controller is a ring-like structure disposed about a finger of the clinician that is engagable by the thumb of the clinician. The imaging controller can include a joystick and/or one or more buttons to allow the clinician to redirect the viewpoint of an image capturing device. In some embodiments, the imaging controller includes a controller disposed on the palm of the hand of clinician that is engagable by a digit of the clinician. The imaging controller can include a flexible electronic tattoo with discrete electrical components that are attached to a flexible structure. The controller can be disposed on or within a glove that is worn by the clinician.

Referring to FIG. 1, a robotic surgical system 1 in accordance with the present disclosure is shown generally as a robotic system 10, a processing unit 30, and a user interface 40. The robotic system 10 generally includes linkages or arms 12 and a robot base 18. The arms 12 moveably support a tool 20 having an end effector 22 which is configured to act on tissue. The arms 12 each have an end 14 that supports tool 20. In addition, the ends 14 of the arms 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the arms 12 and/or include data captured by imaging devices that are positioned about the surgical theater (e.g., an imaging device positioned within the surgical site "S", an imaging device positioned adjacent the patient, imaging device 56 positioned at a distal end of an imaging linkage or arm 52). The imaging devices (e.g., imaging devices 16, 56) may capture visual images, infra-red images, ultrasound images, X-ray images, thermal images, and/or any other known images of the surgical site "S". The imaging device 56 can be an endoscope attached to the imaging linkage 52 that is controllable by the clinician as detailed below. The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 43 which are supported on control arms 42 which allow a clinician to manipulate the robotic system 10 (e.g., move the arms 12, the ends 14 of the arms 12, and/or the tools 20). Each of the input handles 43 is in communication with the processing unit 30 to transmit control signals thereto and to receive feedback signals therefrom. Additionally or alternatively, each of the input handles 43 may include input devices 60 which allow the surgeon to manipulate (e.g., clamp, grasp, fire, open, close, rotate, thrust, slice, etc.) the end effectors 22 of the tools 20 supported at the ends 14 of the arms 12.

Each of the input handles 43 is moveable through a predefined workspace to move the ends 14 of the arms 12 within a surgical site "S". The three-dimensional images on the display device 44 are orientated such that movement of the input handle 43 moves the ends 14 of the arms 12 as viewed on the display device 44. It will be appreciated that the orientation of the three-dimensional images on the display device may be mirrored or rotated relative to view from above the patient. In addition, it will be appreciated that the size of the three-dimensional images on the display device 44 may be scaled to be larger or smaller than the actual structures of the surgical site "S" permitting a clinician to have a better view of structures within the surgical site "S". As the input handles 43 are moved, the tools 20, and thus the end effectors 22, are moved within the surgical site "S" as detailed below. As detailed herein, movement of the tools 20 may also include movement of the ends 14 of the arms 12 which support the tools 20.

For a detailed discussion of the construction and operation of a robotic surgical system 1, reference may be made to U.S. Pat. No. 8,828,023, the entire contents of which are incorporated herein by reference.

Figure 2:
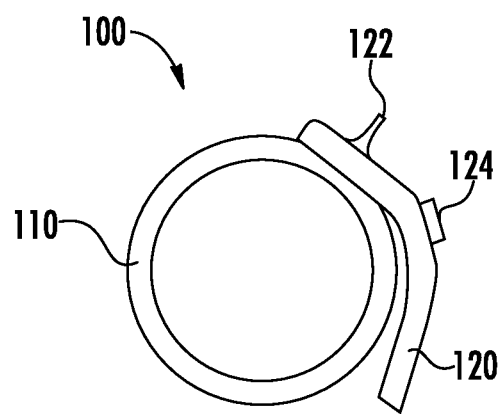
FIG. 2 is a side view of an exemplary imaging controller of the user interface of FIG. 1 in accordance with the present disclosure.

With additional reference to FIG. 2, the user interface 40 includes an image controller 100 provided in accordance with the present disclosure. The image controller 100 is in communication with the processing unit 30 to operate the imaging device 56 and/or the imaging linkage 56 such that a representation or image of the surgical site on the display 44 is manipulated by the image controller 100. The image controller 100 can be in wired or wireless communication with the processing unit 30. When the image controller 100 is in wired communication with the processing unit 30, the image controller 100 can include a wire (not shown) that plugs into the control arm 42 or the input handle 43.

The image controller 100 includes an attachment member 110 and an interface 120. The attachment member 110 is configured to secure the image controller 100 to the finger of a clinician. As shown, the attachment member is in the form of an adjustable ring that fits over the index finger of a clinician. It is envisioned that the attachment member 110 can secure to more than one finger or a digit other than the index finger.

The interface 120 includes a first controller 122 and a second controller 124. While two controllers are shown and described, it is contemplated that any number of controllers may be provided, in accordance with the present disclosure. The interface 120 is secured to the attachment member 110 such that the first and second controllers 122, 124 are accessible by the thumb of the same hand of the clinician as the index finger which the attachment member 110 is secured. The first controller 122 is in the form of a joystick extending outward from the surface of the interface 120. The second controller 124 is in the form of a button or a switch that has first and second positions. When the second controller 124 is a button it is undepressed in the first position and depressed in the second position.

The first controller 122 has first and second modes. When the second controller 124 is in the first position, the first controller is in the first mode in which engagement of the first controller 122 operates the imaging device 52 such that a graphical representation of the surgical site as shown on the display 44 pans in a direction that the first controller 122 is moved. For example, when the first controller 122 is pushed to the up in the first mode, the imaging device 52 moves such that the graphical representation of the surgical site on the display 44 pans to the up. When the second controller 124 is in the second position, the first controller is in the second mode in which engagement of the first controller 122 rotates and zooms the imaging device 56 such that the graphical representation of the surgical site rotates or zooms. For example, when the first controller 122 is pushed up in the second mode, the imaging device 56 moves towards the surgical site or zooms towards the surgical site such that the graphical representation of the surgical site on the display 44 zooms in. It is envisioned that the imaging device 56 may physically move in response to the engagement of the first controller 122 and/or internal components of the imaging device 56 may move to modify the graphical representation of the surgical site as detailed above.

Figure 3:
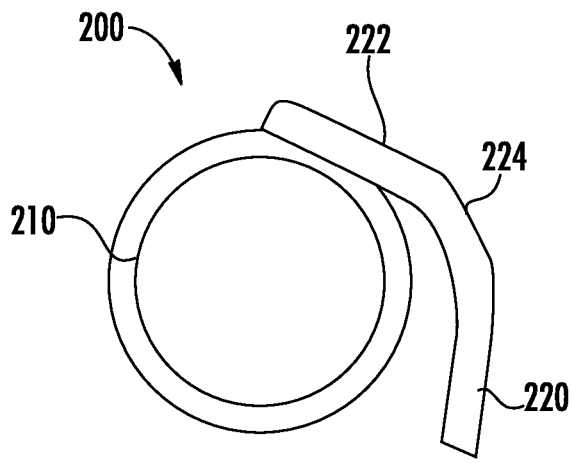
FIG. 3 is a side view of another imaging controller for use with the user interface of FIG. 1 in accordance with the present disclosure.

Referring now to FIG. 3, another image controller 200 is provided in accordance with the present disclosure. The image controller 200 is similar to the image controller 100 detailed above, as such, only the differences will be detailed herein for reasons of brevity. The image controller 200 includes an attachment member 210 and an interface 220 similar to the attachment member 110 and the interface 120 of the image controller 100, respectively.

The interface 220 includes first and second touch sensitive controllers 222, 224. Each of the first and second controllers 222, 224 receive input swipes from a clinician. It is envisioned that the first controller 222 functions in a similar manner to the first controller 122 in the first mode and the second controller 224 functions in a similar manner to the first controller in the second mode. For example, when the first controller 222 is swiped up, the imaging device 56 moves such that a graphical representation on the display 44 pans up and when the second controller 224 is swiped up, the imaging device 56 moves such that the graphical representation on the display 44 zooms in.

Figure 4:
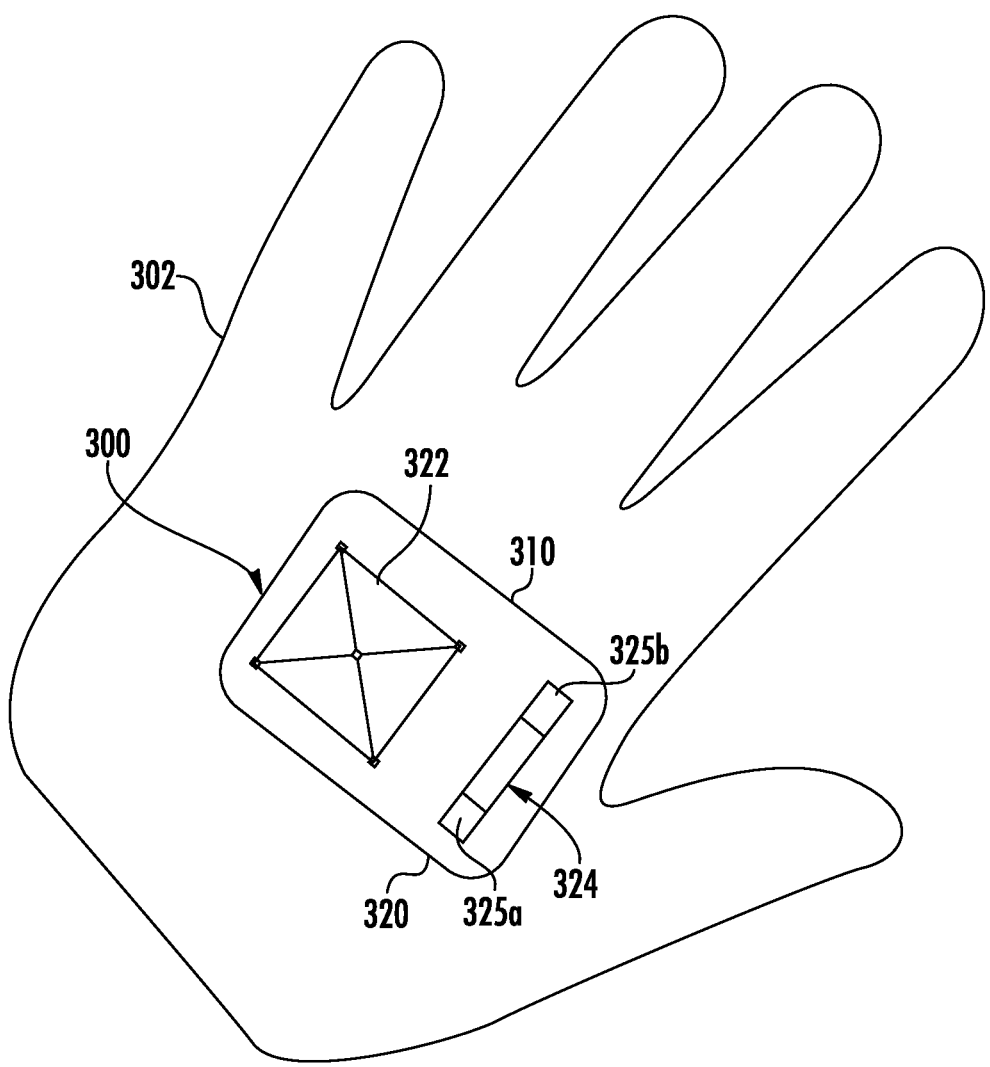
FIG. 4 is a side view of another imaging controller for use with the user interface of FIG. 1 in accordance with the present disclosure.

Referring now to FIG. 4, another image controller 300 is provided in accordance with the present disclosure. The image controller 300 is in the form of a flexible electronic tattoo that is disposed on the palm of a clinician. The image controller 300 may be directly attachable to a hand of a clinician, attachable to a glove 302 worn by a clinician, or integrated into the palm of a glove 302 worn by a clinician. When the image controller 300 is directly attached to a hand of a clinician or on the glove 302, the image controller 300 can include an attachment member 310 in the form of an adhesive layer and when the image controller 300 is integrated into the palm of a glove 302 the glove 302 can be the attachment member. The image controller 300 includes an interface 320 that supports a first controller 322 and a second controller 324 that are engagable by one or more fingers of a hand of clinician on which the image controller 300 is disposed.

The first and second controllers 322 and 324 can have various configurations to operate functions of the imaging device 56. For example, the first and second controllers 322, 324 can have a configuration similar to the first and second controllers 122, 124 in which the first controller 322 is a touch sensitive area that receives swipes from a finger of the clinician and the second controller 324 has a first position and a second position. The second controller 324 can be touch sensitive such that a swipe in a first direction sets the second controller 324 in the first position and a swipe in a second direction opposite the first direction set the second controller 324 in the second position. The second controller 324 can have first and second indicators 325a, 325b that provide indicia as to the position of the second controller 324. For example, when the second controller 324 is in the first position, the first indicator 325a is illuminated and when the second controller 324 is in the second position, the second indicator 325b is illuminated. Alternatively, the first and second controllers 322, 324 can have a configuration similar to the first and second controllers 222, 224 in which the first controller 322 receives swipes to operate panning functions of imaging device 56 and the second controller 324 receives swipes to operate rotating and zooming functions of the imaging device 56.

The image controllers 100, 200, 300 detailed above can be single use or reusable. In addition, the image controllers 100, 200, 300 detailed above can be sterile or non-sterile. Further, while detailed above for use during a robotic surgical procedure, it is envisioned that the image controllers 100, 200, 300 detailed herein could be used in a variety of application including, but not limited to, laparoscopic surgical procedures, endoscopic surgical procedures. It is contemplated that the image controllers 100, 200, 300 can be used in areas outside of surgical procedures where ones hands are used to control a device and it would be beneficial to adjust a camera or a view provided by a camera. For example, the image controllers 100, 200, 300 could be used to control a camera attached to a drone.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A robotic surgical system comprising:
   a processing unit;
   a surgical robot configured to receive commands from the processing unit, the surgical robot including:

a first tool supported by a first linkage; and an imaging device supported by an imaging linkage; and a user interface in communication with the processing unit and is configured to operate the surgical robot, the user interface including;

a display;

a first control arm configured to operate the first tool; and an image controller including an attachment member and an interface, the attachment member configured to secure the image controller to a hand of a clinician engaged with the first control arm, the interface including a first controller configured to operate the imaging device to manipulate a graphical representation on the display.

2. The robotic surgical system according to claim 1, wherein the image controller is in wireless communication with the processing unit.

3. The robotic surgical system according to claim 1, wherein the surgical robot includes a second tool supported by a second linkage and the user interface includes a second control arm configured to operate the second tool.

4. The robotic surgical system according to claim 3, wherein first control arm operates the first tool, the second control arm operates the second tool, and the image controller operates the imaging device simultaneously and independent of one another.

5. A method of operating an imaging device of a robotic surgical system, the method comprising:

engaging a control arm of a user interface with a hand to operate a first tool of a surgical robot; and engaging an image controller with a digit of the hand engaged with the control arm to operate an imaging device of the surgical robot, the image controller attached to the hand of the clinician.

6. The method according to claim 5, wherein engaging the image controller with the digit of the hand engaged with the control arm includes engaging the image controller with a digit of the hand engaged with the control arm.

7. The method according to claim 5, wherein engaging the image controller with the digit of the hand engaged with the control arm includes engaging the image controller with a thumb of the hand engaged with the control arm, the image controller supported on another part of the hand.

* * * * *